United States Patent
Burnett (10) Patent No.: US 10,847,268 B1
(45) Date of Patent: Nov. 24, 2020

(54) PATIENT INFORMATION EXCHANGE SYSTEM AND ASSOCIATED METHODS

(71) Applicant: Government of the United States, as represented by the Secretary of the Air Force, Wright-Patterson AFB, OH (US)

(72) Inventor: Gregory M. Burnett, Dayton, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 101 days.

(21) Appl. No.: 16/192,863

(22) Filed: Nov. 16, 2018

Related U.S. Application Data (60) Provisional application No. 62/623,791, filed on Jan. 30, 2018.

(51) Int. Cl.
*G16H 80/00* (2018.01)
*H04L 29/06* (2006.01)
*G16H 10/60* (2018.01)

(52) U.S. Cl.
CPC ............ *G16H 80/00* (2018.01); *G16H 10/60* (2018.01); *H04L 63/083* (2013.01)

(58) Field of Classification Search
CPC .............................................. G06Q 50/22–24
See application file for complete search history.

(56) References Cited

U.S. PATENT DOCUMENTS

| | | | | |
|---|---|---|---|---|
| 2002/0052539 A1* | 5/2002 | Haller | ............... | A61B 5/0031 600/300 |
| 2002/0165912 A1* | 11/2002 | Wenocur | ............... | H04L 63/126 709/203 |
| 2003/0009244 A1* | 1/2003 | Engleson | ............... | G16H 20/17 700/86 |
| 2004/0030586 A1* | 2/2004 | Cucchiara | ............... | G06Q 10/10 705/3 |
| 2008/0228045 A1 | 9/2008 | Gao et al. | | |
| 2010/0219241 A1 | 9/2010 | Corwin et al. | | |

(Continued)

OTHER PUBLICATIONS

Department of Defense, "Guidelines for Engineering, Manufacturing and Maintenance Documentation Requirements for Item Unique Identification (IUID) Implementation," Version 1.2, Apr. 20, 2007.

(Continued)

*Primary Examiner* — Neal Sereboff
(74) *Attorney, Agent, or Firm* — AFMCLO/JAZ; Timothy M. Barlow (57) ABSTRACT

Systems and associated methods for offline data transfer using exclusive point-to-point data communication between a transference device and a reception device. The transference device comprises an outputting subsystem configured to maintain a patient-specific chain-of-care data packet comprising patient-related identification data, health data, and sensor communication data. The transference device encodes the chain-of-care data packet in a machine-readable form (e.g, matrix barcode, haptic pulse, audio signal) that is detected by an appropriate component of the proximately-positioned reception device (e.g., camera, accelerometer, microphone) and decoded to create a cloned chain-of-care packet and to reestablish sensor communication for the subject patient through the reception device.

1 Claim, 6 Drawing Sheets

(56) References Cited

U.S. PATENT DOCUMENTS

| | | | |
|---|---|---|---|
| 2013/0035571 A1 | 2/2013 | Moure Alonso et al. | |
| 2013/0054271 A1 | 2/2013 | Langford et al. | |
| 2014/0067426 A1* | 3/2014 | Neff | H04W 4/80 |
| | | | 705/3 |
| 2015/0026785 A1 | 1/2015 | Soon-Shiong | |
| 2016/0231718 A1 | 8/2016 | Logan et al. | |
| 2017/0000407 A1 | 1/2017 | Saxby et al. | |
| 2017/0068785 A1 | 3/2017 | Experton et al. | |
| 2017/0147772 A1 | 5/2017 | Meehan et al. | |
| 2017/0242968 A1 | 8/2017 | Kiukkonen | |
| 2017/0281462 A1 | 10/2017 | Freeman et al. | |
| 2017/0296107 A1* | 10/2017 | Reid | A61B 5/0022 |
| 2018/0039737 A1* | 2/2018 | Dempers | G06F 19/00 |
| 2018/0217971 A1* | 8/2018 | Safavi | G06K 7/1417 |

OTHER PUBLICATIONS

International Civil Aviation Organization, Machine Readable Travel Documents,: Part 1, vol. 2, 6th edition, 2006.

ISO/IEC 7816-4, "Identification cards—Integrated circuit cards Part 4: Organization, security and commands for interchange," Second edition, Jan. 15, 2005.

Cooper et al., "Interfaces for Personal Identity Verification—Part 1: PIV Card Application Namespace, Data Model and Representation," NIST Special Publication 800-73-4, May 2015.

* cited by examiner

PATIENT INFORMATION EXCHANGE SYSTEM AND ASSOCIATED METHODS

PRIORITY

Pursuant to 37 C.F.R. § 1.78(a)(4), this application claims the benefit of and priority to prior filed Provisional Application Ser. No. 62/623,791, filed 30 Jan. 2018, which is expressly incorporated herein by reference.

STATEMENT OF GOVERNMENT INTEREST

The invention described herein may be manufactured, used, and licensed by or for the Government of the United States for all governmental purposes without the payment of any royalty.

BACKGROUND

Emergency medical services (EMS), also known as ambulance services or paramedic services, involves treatment of illnesses and injuries that require an urgent medical response, out-of-hospital treatment, and transport to definitive care. In civilian health care practice, Emergency Medical Technicians (EMTs) are the most common providers of EMS. The military counterpart to the civilian EMS provider/EMT is the combat medic, who is trained to perform many of the same tasks as civilian EMTs such as administer inoculations, take patient histories, document medical interventions and products administered (e.g., medications, fluids), perform cardiopulmonary resuscitation (CPR), apply wound dressing/bandaging, and stabilize broken bones. In addition, combat medics are trained to provide medical assistance in combat situations requiring trauma care that is typically beyond the training level of a civilian EMS provider, such as battlefield transfusions and advanced lifesaving techniques.

Dismounted medics are defined hereinafter as those medics called upon to separate from special medical support vehicles to provide medical assistance in combat situations, often in a far-forward and/or austere environment. In this role, dismounted medics are often required to "hand-off" patients to the next level of care or amongst other dismounted medics. Unfortunately, battlefield and environmental factors during such hand-off may complicate the seamless transfer of patient documentation as well as control of medical sensors connected to and reporting live vital signs associated with a given patient.

The typical patient hand-off process relies heavily on physical paper documentation and/or verbal discussion among responsibility-exchanging care providers. Paper, often in the form of a triage card, is prone to damage from the environment (e.g., rain, dusk, mud, blood) and often is too time consuming for the responsible combat medic to reliably and legibly fill out. Moreover, paper documentation does not force combat medics to follow a standard of entry, thus rendering the documentation difficult to interpret at the next level of care.

What is needed is improved systems and/or methods to expedite the in-field digital hand-off of patient care documentation and real-time, streaming connected patient physiological sensors between elements along the chain of care.

SUMMARY

The present invention overcomes the foregoing problems and other shortcomings, drawbacks, and challenges of medical patient data control and transfer. While the invention will be described in connection with certain embodiments, it will be understood that the invention is not limited to these embodiments. To the contrary, this invention includes all alternatives, modifications, and equivalents as may be included within the spirit and scope of the present invention.

According to one embodiment of the present invention, a method of offline data transfer using exclusive point-to-point data communication between a transference device and a reception device comprises: receiving, using the transference device, a first chain-of-care data packet comprising at least one of patient-related identification data, patient-related health data, and sensor-specific communication data; encoding, using the transference device, the first chain-of-care data packet to define a machine-readable data representation; outputting, using the transference device, the machine-readable data representation; inputting, using the reception device, the machine-readable data representation; and decoding, using the reception device, the machine-readable data representation to define a second chain-of-care packet substantively equal to the first chain-of-care packet.

According to a first variation of the embodiment described above, the outputting the machine-readable data representation further comprises at least one of: displaying, using the transference device, an optical label; producing, using the transference device, a haptic pulse; and sounding, using the transference device, an audio tone.

The encoding of the first chain-of-care packet may further comprise creating, using the transference device, a string representation of the first chain-of-care packet to define a record string; compressing, using the transference device, the record string to define a byte stream; encrypting, using the transference device, the byte stream to define an encrypted byte stream; and encoding, using the transference device, the encrypted byte stream to define the optical label.

The inputting of the machine-readable data representation may further comprise at least one of: scanning, using the reception device, the optical label; detecting, using the reception device, the haptic pulse; and perceiving, using the reception device, the audio tone.

According to another variation of the embodiment, the method further comprises: terminating, using the transference device, a first sensor-specific communication channel characterized by the sensor-specific communication data of the first chain-of-care data packet; and initiating, using the reception device, a second sensor-specific communication channel characterized by the sensor-specific communication data of the second chain-of-care data packet.

According to a further variation of the embodiment, the method further comprises encoding the first chain-of-care data packet upon detecting, using the transference device, a transfer request of a transfer signal type selected from the group consisting of an audio signal, a wireless emission signal, and a wired signal.

According to another variation of the embodiment, the method further comprises detecting, using the reception device, a reception request of a reception signal type selected from the group consisting of an audio signal, a wireless emission signal, and a wired signal.

According to a further variation of the embodiment, the first chain-of-care data packet further comprises at least one of transfer session control authentication data and transference device user confirmation data.

According to another variation of the embodiment, the sensor-specific communication data of the first chain-of-care data packet further comprises at least one of a MAC address, a sensor name, and an authentication pair code.

According to second embodiment of the invention, an exclusive point-to-point data communication system for offline data transfer comprises: a transference device characterized by a first computer processor and by a first non-transitory computer-readable storage medium comprising a first plurality of instructions which, when executed by the first computer processor, is configured to: receive a first chain-of-care data packet comprising at least one of patient-related identification data, patient-related health data, and sensor-specific communication data; encode the first chain-of-care data packet to define a machine-readable data representation; and output the machine-readable data representation; and a reception device characterized by a second computer processor and by a second non-transitory computer-readable storage medium comprising a second plurality of instructions which, when executed by the second computer processor, is configured to: input the machine-readable data representation; and decode the machine-readable data representation to define a second chain-of-care packet substantively equal to the first chain-of-care packet.

According to a first variation of the embodiment, the first plurality of instructions are configured to output the machine-readable data representation is further configured to at least one of: display an optical label; produce a haptic pulse; and sound an audio tone.

According to another variation of the embodiment, the first plurality of instructions configured to encode the first chain-of-care packet is further configured to: create a string representation of the first chain-of-care packet to define a record string; compress the record string to define a byte stream; encrypt the byte stream to define an encrypted byte stream; and encode the encrypted byte stream to define the optical label.

According to a further variation of the embodiment, the second plurality of instructions configured to input the machine-readable data representation is further configured to at least one of: scan the optical label; detect the haptic pulse; and perceive the audio tone.

According to another variation of the embodiment, the first plurality of instructions is further configured to terminate a first sensor-specific communication channel of the transference device characterized by the sensor-specific communication data of the first chain-of-care data packet; and where the second plurality of instructions is further configured to initiate a second sensor-specific communication channel of the reception device characterized by the sensor-specific communication data of the second chain-of-care data packet.

According to a further variation of the embodiment, the first plurality of instructions is configured to receive a transfer request of a transfer signal type selected from the group consisting of an audio signal, a wireless emission signal, and a wired signal.

According to another variation of the embodiment, the second plurality of instructions is configured to receive a reception request of a reception signal type selected from the group consisting of an audio signal, a wireless emission signal, and a wired signal.

According to a further variation of the embodiment, the first chain-of-care data packet further comprises at least one of transfer session control authentication data and transference device user confirmation data.

According to another variation of the embodiment, the sensor-specific communication data of the first chain-of-care data packet further comprises at least one of a MAC address, a sensor name, and an authentication pair code.

According to a third embodiment of the invention, an offline data transfer device comprises: a computer processor and a non-transitory computer-readable storage medium comprising a plurality of instructions which define at least one of an outputting subsystem and an inputting subsystem; where the outputting subsystem, when executed by the computer processor, is configured to: receive a first chain-of-care data packet comprising at least one of patient-related identification data, patient-related health data, and sensor-specific communication data; encode the first chain-of-care data packet to define a machine-readable data representation; and output the machine-readable data representation; and where the inputting subsystem, when executed by the computer processor, is configured to: input the machine-readable data representation; and decode the machine-readable data representation to define a second chain-of-care packet substantively equal to the first chain-of-care packet.

According to a first variation of the embodiment, the outputting subsystem configured to output the machine-readable data representation is further configured to at least one of: display a first optical label; produce a first haptic pulse; and sound a first audio tone; where the inputting subsystem configured to input the machine-readable data representation is further configured to at least one of: scan a second optical label; detect a second haptic pulse; and perceive a second audio tone; where the outputting subsystem is further configured to terminate a first sensor-specific communication channel of the transference device characterized by the sensor-specific communication data of the first chain-of-care data packet; and where the inputting subsystem is further configured to initiate a second sensor-specific communication channel of the reception device characterized by the sensor-specific communication data of the second chain-of-care data packet.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings provide visual representations which will be used to more fully describe various representative embodiments and can be used by those skilled in the art to better understand the representative embodiments disclosed and their inherent advantages. The drawings are not necessarily to scale, emphasis instead being placed upon illustrating the principles of the devices, systems, and methods described herein. In these drawings, like reference numerals may identify corresponding elements.

DETAILED DESCRIPTION

Specific embodiments of the disclosure will now be described in detail with reference to the accompanying figures. While this invention is susceptible of being embodied in many different forms, there is shown in the drawings and will herein be described in detail specific embodiments, with the understanding that the present disclosure is to be considered as an example of the principles of the invention and not intended to limit the invention to the specific embodiments shown and described. In the description below, like reference numerals may be used to describe the same, similar or corresponding parts in the several views of the drawings.

The present disclosure relates generally to a method of transferring patient and sensor information between mobile end user devices using proximity-based data representations that is conducive to the work environments of both military combat medics and civilian emergency medicine technicians (EMTs). More specifically, the present disclosure is directed to automated sharing of in-field patient care documentation between multiple medics that occurs offline (i.e., requiring no server connection, centralized database, nor internet service connection). The present disclosure also may advantageously provide seamless transfer of control of communication channels between wireless-connected sensors and multiple end user devices (smartphones, digital scanners) and/or computer systems such that ownership of pairing with the sensors may advantageously minimize the loss of real-time streaming sensor data through a mobile, field-conducive hand-off approach.

One embodiment, for example, and without limitation, may comprise a software process that may encode/decode digital patient documentation and also sensor configuration/communication settings through a series of matrix barcodes that may be displayed on a transferor's user device interface and scanned by a receiver's user device interface. The utilization of a bi-directional matrix barcode information exchange process between two physically-proximate end user devices may facilitate a standalone approach to wirelessly share patient information and devices communications settings that mitigates risk of exploitation, thus ensuring secure and controlled hand-off of patient information and sensor pairing used in the care of a patient. Such automation may advantageously discipline the transition of patients along a chain-of-care in an austere environment.

Figure 1:
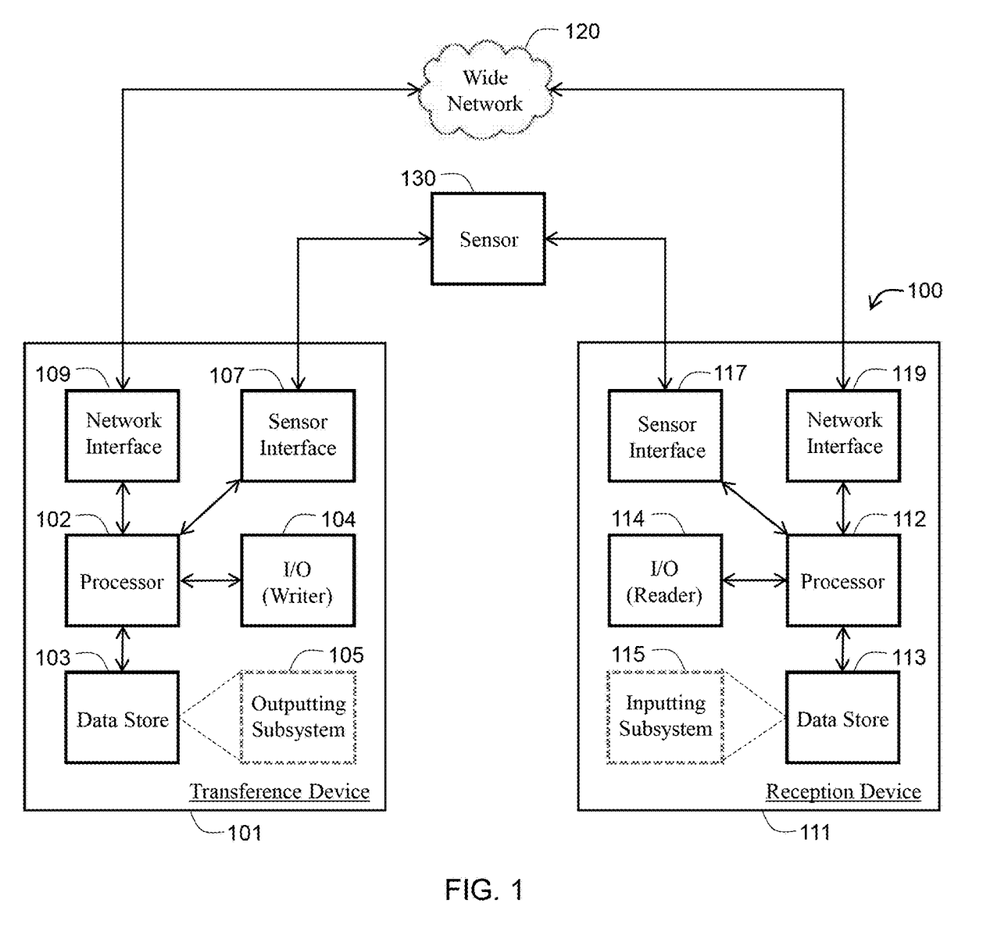
FIG. 1 illustrates an example patient information exchange system (PIES), in accordance with embodiments of the disclosure.

The block diagram of FIG. 1 illustrates an example of the present disclosure's Patient Information Exchange System (PIES) 100, also referred to as a patient data transfer system or simply as a data exchange system, in accordance with embodiments of the disclosure. Those skilled in the art will understand that the principles of the present disclosure may be implemented in any type of suitably arranged device or system (e.g., smartphone, handheld scanner), in any combination. More specifically, the PIES 100, according to an embodiment of the present disclosure, may include a Transference Device 101 and a Reception Device 111. Either or both of the Transference Device 101 and the Reception Device 111 may be configured, either commonly or separately, for data communication with various networked data sources (not shown) via a wide area network 120, such as the Internet. Alternatively, or in addition, the PIES 100 may be configured to advantageously facilitate point-to-point data communication between the Transference Device 101 and the Reception Device 111 without reliance on a common servicing network 120 (for example, in an austere service environment with little or no computing and/or networking service availability).

Continuing to refer to FIG. 1, in more detail, the Transference Device 101 may comprise a processor 102 that may be operable to accept and execute computerized instructions, and also a data store 103 which may store data and instructions used by the processor 102. More specifically, the processor 102 may be positioned in data communication with some number of the networked devices (not shown) and may be configured to direct input from such networked devices to the data store 103 for storage and subsequent retrieval. For example, and without limitation, the processor 102 may be in data communication with external computing resources, such as a patient information data server system, through a direct connection and/or through a network connection to the wide area network 120 facilitated by a network interface 109. Furthermore, the processor 102 may be positioned in data communication with some number of direct-connected devices and may be configured to direct input from such direct-connected devices to the data store 103 for storage and subsequent retrieval. For example, and without limitation, the processor 102 may be in data communication with direct-connected resources, such as a sensor 130 (e.g., patient-connected health monitor), through a direct connection (either wired or wireless) facilitated by a sensor interface 107.

Similarly, the Reception Device 111 may comprise a processor 112 that may be operable to accept and execute computerized instructions, and also a data store 113 which may store data and instructions used by the processor 112. More specifically, the processor 112 may be positioned in data communication with some number of the networked devices (not shown) and may be configured to direct input from such devices to the data store 113 for storage and subsequent retrieval. For example, and without limitation, the processor 112 may be in data communication with external computing resources, such as a patient information data server system, through a direct connection and/or through a network connection to the wide area network 120 facilitated by a network interface 119. Furthermore, the processor 112 may be positioned in data communication with some number of direct-connected devices and may be configured to direct input from such direct-connected devices to the data store 113 for storage and subsequent retrieval. For example, and without limitation, the processor 112 may be in data communication with direct-connected resources, such as the sensor 130 (e.g., patient-connected health monitor), through a direct connection (either wired or wireless) facilitated by a sensor interface 117.

For example, and without limitation, the computerized instructions of the Transference Device 101 may be configured to implement an Outputting Subsystem 105 which may be stored in the data store 103 and retrieved by the processor 102 for execution. The Outputting Subsystem 105 may be operable to read patient-related records from the data store 103 and to encode those data for point-to-point transmission to the Reception Device 111. Also for example, and without limitation, the computerized instructions of the Reception Device 111 may be configured to implement an Inputting Subsystem 115 which may be stored in the data store 113 and retrieved by the processor 112 for execution. The Inputting Subsystem 115 may be operable to decode data received through point-to-point transmission from the Transference Device 101 and to write the decoded data as 'cloned' patient-related records to the data store 113 for subsequent retrieval and processing. Certain embodiments of the Transmitting Device 101 and the Reception Device 111 may provide the point-to-point data communication described herein to discipline hand-off of patient responsibility between two collaborating field medics involved in point-of-injury care in an austere environment. Alternative embodiments of the Transmitting Device 101 and the Reception Device 111 may provide the point-to-point data communication described herein to discipline hand-off of patient responsibility among other providers along the chain-of-care including, but not limited to, first responders, EMS specialists, ambulance treatment and transfer, hospital units, and casualty evacuation (CASEVAC). Support for the disclosed point-to-point data communication by a computing system at a facility, such as a hospital unit or forward operating surgery tent, may equip the medic to have a patient's digital documentation and sensor information "scanned" and merged into the facility's master medical control system for continual care of the patient.

Those skilled in the art will appreciate that the present disclosure contemplates the use of computer instructions and/or systems configurations that may perform any or all of the operations involved in patient information exchange and care management. The disclosure of computer instructions that include Outputting Subsystem 105 instructions and Inputting Subsystem 115 instructions is not meant to be limiting in any way. Also, the disclosure of systems configurations that include Transference Device(s) 101 and Reception Device(s) 111 is not meant to be limiting in any way. Those skilled in the art will readily appreciate that stored computer instructions and/or systems configurations may be configured in any way while still accomplishing the many goals, features and advantages according to the present disclosure.

Figure 2:
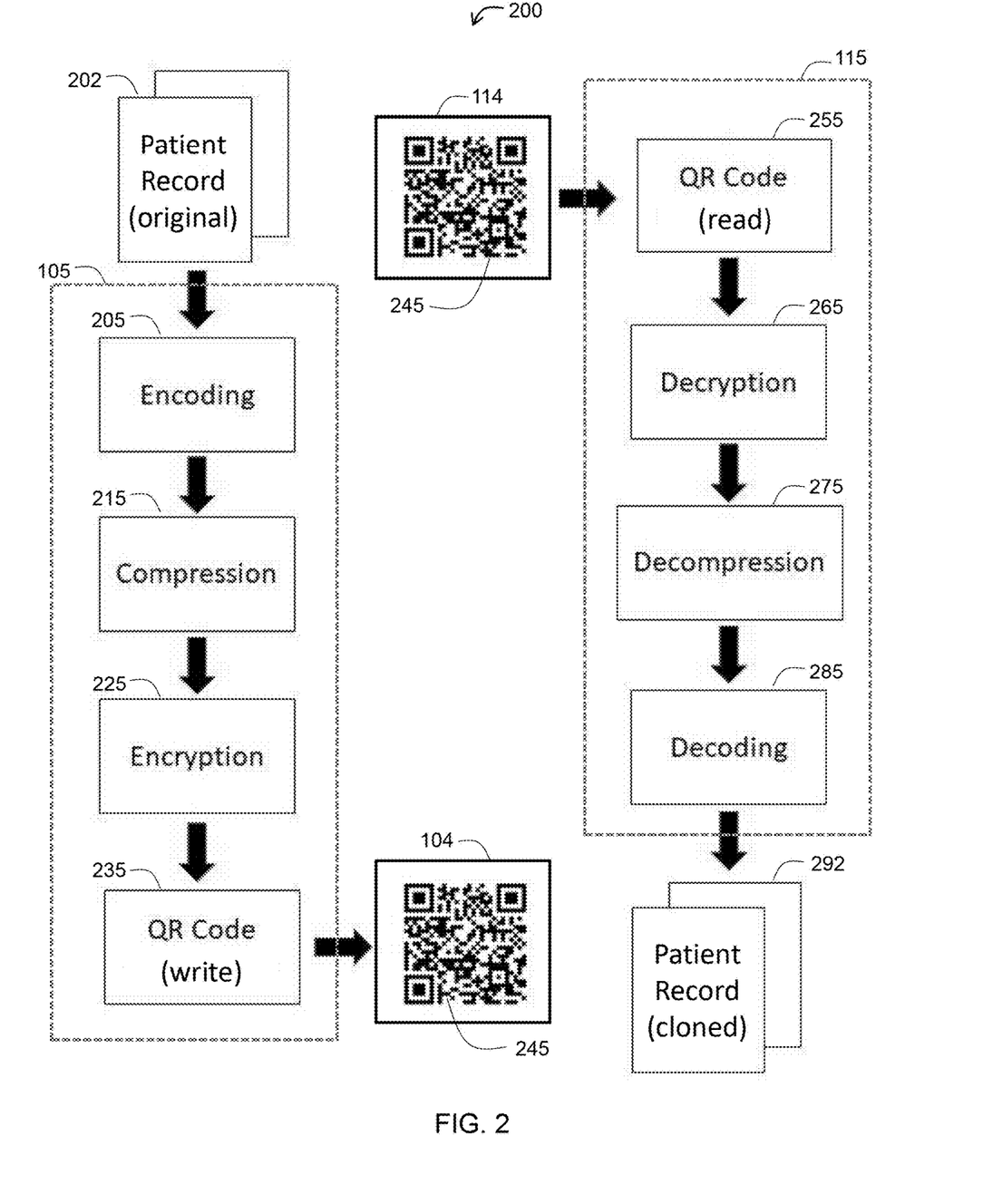
FIG. 2 is a block diagram that illustrates a patient record state transition using the PIES of FIG. 1.

Referring now to FIG. 2, a patient information state transition diagram 200 illustrating an exemplary lifecycle of a data object as it transits the Outputting Subsystem 105 and the Inputting Subsystem 115 described above and in FIG. 1 is presented. In accordance with some representative embodiments, a number of Outputting Subsystem 105 modules such as an Encoding module 205, a Compression module 215, an Encryption module 225, and a Matrix Barcode (write) module 235; and a number of Inputting Subsystem 115 modules such as a Matrix Barcode (read) module 255, a Decryption module 265, a Decompression module 275, and a Decoding module 285 may be employed in this flow, though the workflow may be carried out by other modules operable to provide similar and/or related cooperating transference and reception functionalities.

Still referring to FIG. 2, and continuing to refer to FIG. 1, the PIES 100 may be installed as an add-on application to an electronic patient monitoring tool designed for battlefield use which may comprise software that executes on a smartphone or other mobile and/or handheld device. For example, and without limitation, the Transference Device 101 of the PIES 100 may be configured to receive and write to a local data store patient-related health background information (e.g., name, identification, unit, blood type, allergies, pertinent medical history), and also to draw patient-related real-time health information (e.g., blood pressure and other vital signs) from a wide variety of commercially available, U.S. Food and Drug Administration (FDA)-approved sensors. In accordance with some representative embodiments of the present disclosure, an original Patient Record 202 may comprise the patient-related health background information as augmented by some subset of the patient-related real-time health information. The patient transfer process, as implemented by the Outputting Subsystem 105, may be launched from a transferring user initiation prompt. The PIES 100 may retrieve the Patient Record 202 (e.g., in the form of a digital file or as a database record) and may forward it to the Encoding Module 205. The Encoder Module 205 may encode the record entries using a matrix of coding conventions and expandable word libraries and may render a resultant string representation of the record. The Compression Module 215 may compress the input record string and render a resultant compressed string representation of record in the form of a byte stream. The Encryption Module 225 may employ encryption (e.g., AES 128 bit encryption) to render a resultant encrypted byte stream representation of record. The Matrix Barcode generation (write) Module 235 may create a matrix barcode image from the encrypted byte stream. The Input/Output (IO) Writer 104 may be employed to display the Matrix Barcode Image 245.

Still referring to FIG. 2, and continuing to refer to FIG. 1, the patient transfer process, as implemented by the Inputting Subsystem 115, may be launched from the action of a receiving user positioning the Reception Device 111 for proximity-based, point-to-point data communication with the Transference Device 101. For example, and without limitation, the Input/Output (IO) Reader 114 of the Reception Device 111 may be employed to receive (e.g., scan) the Matrix Barcode Image 245 for processing by the Matrix Barcode generation (read) Module 255 to produce a received byte stream of the Matrix Barcode Image 245. The Decryption Module 265 may apply decryption (e.g., AES 128 bit decryption) using a known hash key to render a Byte Stream representation. The Decompression Module 275 may decompress the input byte stream to render a string representation of a resultant record. The Decoding Module 285 may decode the input string using a matrix of coding conventions and expandable word libraries to render a record (e.g., digital file or database record) in the form of a Cloned Patient Record 292 that is substantively similar to the original Patient Record 202.

Figure 3A:
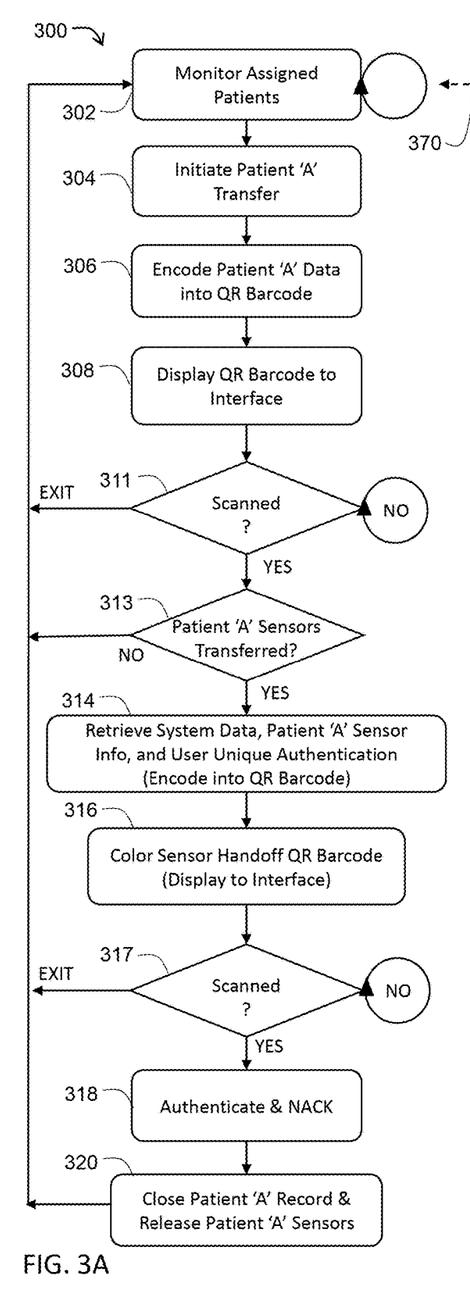
FIG. 3A is a system level functional flowchart illustrating a transference method, in accordance with embodiments of the disclosure.
Figure 3B:
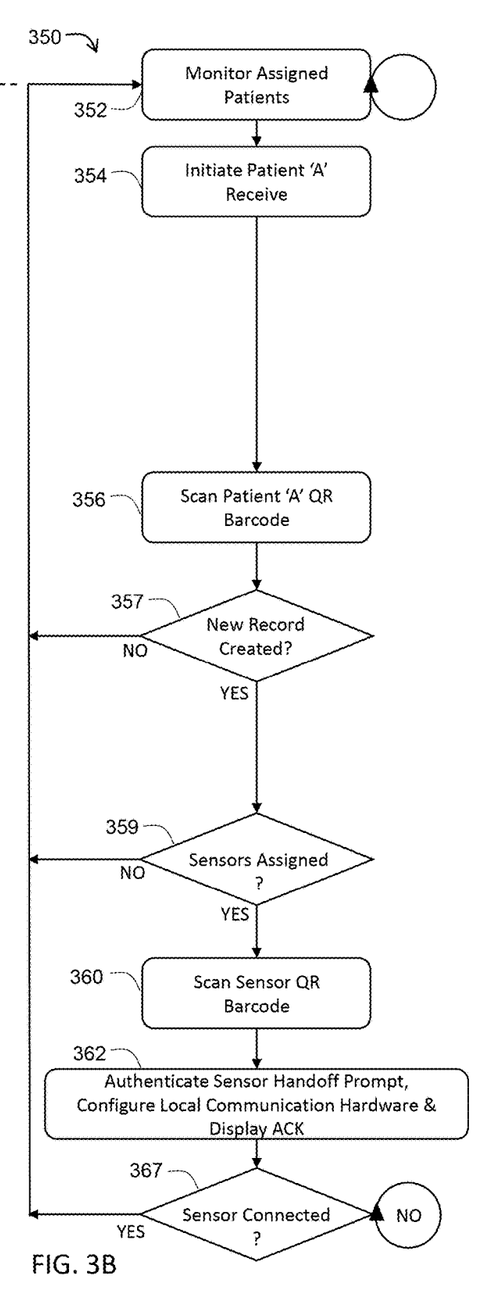
FIG. 3B is a system level functional flowchart illustrating a reception method, in accordance with embodiments of the disclosure.

Referring now to FIGS. 3A and 3B, a method for point-to-point, wireless patient information and sensor communication transfer 300 and reception 350 will now be described in detail. Generally speaking, one embodiment of the disclosure may be configured to employ an embedded camera on a smartphone to "scan" another smartphone's screen displaying a series of matrix barcodes representing patient documentation and sensor communication settings. Additional transfer control operations may include hand-off session control authentication and user confirmation. The transfer control process may be implemented in computer software instructions for use on mobile devices, computer systems, standalone or connected systems. The embodiments described herein may be used at the point-of-injury to exchange information created and controlled by one medic to another medic through a series of bi-directional matrix barcodes. This process may advantageously allow the seamless exchange of information without the added cost of connecting additional hardware to a mobile device, but rather may exploit existing field tool architectures (including hardware and software) currently underutilized by dismounted medics.

Referring more specifically to FIGS. 3A and 3B, the Transference Device 101 may execute the PIES 100 at Block 302 to maintain patient-related records for an assigned patient (referred to hereinafter as Patient 'A') using, for example, and without limitation, patient information and connected sensor information associated with Patient 'A'. At Block 304, a user of Transference Device 101 may initiate transfer of monitoring responsibility for Patient 'A' to another device configured to execute a separate instance of the PIES 100. To enable such transfer, the Transference Device 101 may encode Patient 'A' data into a matrix barcode (Block 306) and may project the matrix barcode to an interface (e.g., display) on Transference Device 101 (Block 308). If, at Block 311, the Transference Device 101 does not detect scanning of the displayed matrix barcode by a candidate device for purposes of receiving monitoring responsibility, the PIES 100 on the Transference Device 101 may return to monitoring of assigned patients at Block 302 as normal (e.g., "exit" on timeout).

The Reception Device 111 may serve as the candidate device configured to receive monitoring responsibility for Patient 'A'. More specifically, while potentially monitoring patient information and connected sensor information associated with other assigned patients (Block 352), the Reception Device 111 user may prompt the PIES 100 to initiate a receive operation to assume monitoring responsibility for Patient 'A' (Block 354). At Block 356, patent-related data from Transference Device 101 may be accessed by Reception Device 111 by, for example, and without limitation, scanning of the matrix barcode using the reader interface of the Reception Device 111. If, at Block 357, a new patient record is successfully created on the Reception Device 111 from the received matrix barcode, the Reception Device 111 may use its interface to flag the successful scanning operation (Block 357).

If, at Block 311, the Transference Device 101 detects successful scanning of the displayed matrix barcode by the Reception Device 111, the PIES 100 on the Transference Device 101 may then determine if Patient 'A' sensors are available and/or desired for transfer to Reception Device 111 (Block 313). If so, the Transference Device 101 may retrieve system data related to Transference Device 101 itself, Patient 'A' sensor information, and/or unique authentication for the Transference Device 101 user and may encode the same into a second matrix barcode (Block 314). At Block 316, this sensor handoff matrix barcode may be displayed to the writer interface on the Transference Device 101. For example, and without limitation, the sensor handoff matrix barcode may display as a different color from the previously-displayed patient-information matrix barcode to visually distinguish the two barcodes for the benefit of the respective users of the Transference Device 101 and the Reception Device 111.

If Patient 'A' sensors are available and/or desired for transfer to Reception Device 111 (Block 359), sensor data from Transference Device 101 may be accessed by Reception Device 111 by, for example, and without limitation, scanning of the sensor matrix barcode using the reader interface of the Reception Device 111 (Block 360). At Block 362, the Reception Device 111 may use the sensor-specific information decoded from the sensor matrix barcode to authenticate the sensor handoff from the Transference Device 101, to configure and initiate data communication with the sensor, and to display an acknowledgement to signal successful transfer of control of the sensor to the Reception Device 111. Once the sensor is successfully connected (Block 367), the Reception Device 111 may return to monitoring mode for assigned patients (Block 352) while it awaits the next opportunity to initiate another patient receive action (Block 354) and/or to initiate a patient transfer action (Block 302 via logic path 370). More specifically, for example, and without limitation, any device executing the PIES 100 may be configured to take on the role of either a Transference Device 101 and/or a Reception Device 111.

If, at Block 317, the Transference Device 101 does not detect scanning of the displayed sensor matrix barcode by the Reception Device 111, the PIES 100 on the Transference Device 101 may return to monitoring of assigned patients at Block 302 as normal (e.g., "exit" on timeout). Alternatively, if the Transference Device 101 does detect successful scanning of the displayed sensor matrix barcode by the Reception Device 111, the PIES 100 on the Transference Device 101 may then process the authentication detected from the Reception Device 111 (Block 318) and may respond by closing the Patient 'A' record on the Transference Device 101 and releasing data communication connectivity with the Patient 'A' sensors (Block 320) before returning to monitoring of any patients still assigned to the Transference Device 101 (Block 302).

Figure 4:
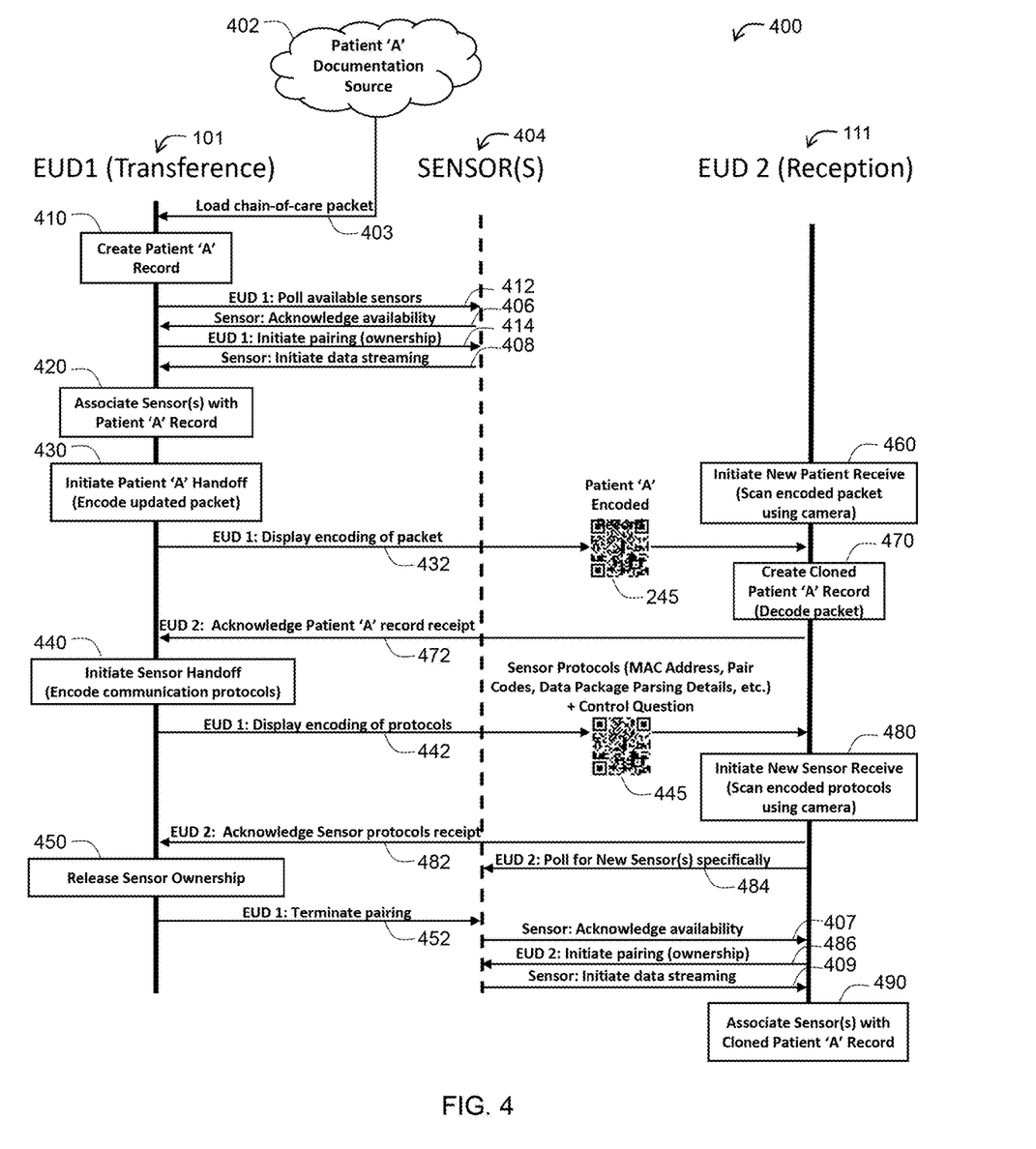
FIG. 4 is a system level communication diagram illustrating matrix barcode-based interaction among components of the PIES of FIG. 1.

Referring now to FIG. 4, a specific example of an implementation of a PIES 100 will now be characterized in detail in the form of a communication diagram 400 showing a first end user device in the role of a Transference Device 101 (hereinafter EUD1), a second end user device in the role of a Reception Device 111 (hereinafter EUD2), and at least one sensor 404. EUD1 may download an external data source 402 a chain-of-care packet 403, defined as, for example, and without limitation, identification and/or medical history documentation for a subject patient (hereinafter referred to as Patient 'A'). EUD1 may then use the PIES 100 to create a local record for Patient 'A' comprising data from the chain-of-care packet (see Block 410). EUD1 may then poll available sensors 412 which, in the example case, may include the sensor 404, to initiate data communication related to Patient 'A' between EUD1 and the sensor 404. After the sensor 404 acknowledges availability to communicate 406, EUD1 may initiate pairing 414 to establish ownership of a data communication channel with the sensor 404, and the sensor 404 may initiate data streaming 408 (e.g., passing of vital signs collected from Patient 'A' to EUD1 for collection and/or further processing). At Block 420, EUD1 may update the Patient 'A' record to associate available sensors (in the example, sensor 404) with that record.

At Block 430, EUD1 may initiate passing of patient-related information for Patient 'A' onto another device, system, and/or personnel. For example, and without limitation, prompting of EUD1 to initiate such data handoff may be in the form of an external request for patient-related information received via audio signal (e.g., wireless or wired), wireless emission signal (e.g., NFC, WiFi, Bluetooth, UWB), wired signal (e.g., USB, Serial, Magnetic, etc.), or a visual display. In response to the prompting, EUD1 may prompt its user to verify an action to encode for transfer patient-related information for a given assigned patient (in the example case, Patient 'A'). Upon user approval, the PIES 100 on EUD1 may then generate a matrix barcode (Block 430) comprising pertinent data from the updated chain-of-care packet for Patient 'A' and may display 432 the encoded data matrix barcode 245 on the EUD1 interface (e.g., smartphone screen).

Still referring to FIG. 4, a user of the PIES 100 executed on EUD2 may initiate (at Block 460) reception of a subject patient(s) information from EUD1 via use of an EUD2 interface (e.g., scanner/camera) to scan the matrix barcode containing, in the illustrated example, the encoded chain-of-care packet for Patient 'A'. For example, and without limitation, the PIES 100 on EUD2 may acknowledge back to EUD1 successful receipt 472 of the matrix barcode, and/or may prompt its user for permission to create a new patient data record after successful scanning EUD1's matrix barcode. Given appropriate permissions, the PIES 100 on EUD2 may decode the matrix barcode and create from it a Patient 'A' record, defined herein as a 'cloned' record, the may comprise some subset of the original chain-of-care packet gathered on EUD1 (Block 470).

In the example case of FIG. 4, successful passing of patient-related information from EUD1 to EUD2 may be followed by similar passing of patient-related sensor information. For example, and without limitation, the PIES 100 on EUD1 may prompt its user to ask if connected sensors for Patient 'A' are to be transferred as well. If so, at Block 440 the PIES 100 on EUD1 may collect all sensor configuration data to include, for example, but without limitation, MAC Address, sensor name, authentication pair codes, end user device system information and unique medic (e.g., EUD1 user) authentication data for permissions to transfer to EUD2 ownership of data communication with, in the example case, sensor 404. Upon user approval, the PIES 100 on EUD1 may then generate a sensor matrix barcode (Block 440) comprising sensor configuration details/protocols and may display 442 the encoded sensor matrix barcode 445 on the EUD1 interface (e.g., smartphone screen). As described above, the PIES 100 on EUD1 may display the sensor matrix barcode in a different color than the previous patient-information matrix barcode to not only indicate that a sensor transfer has been initiated, but also to visually distinguish the two separate transfer actions to the human eye.

Similar to the patient information transfer action described above, the user of the PIES 100 executed on EUD2 may initiate (at Block 480) reception of the transferring sensor configuration information from EUD1 via use of the EUD2 interface (e.g., scanner/camera) to scan the sensor matrix barcode containing, in the illustrated example, the configuration/protocol information for sensor 404. For example, and without limitation, the PIES 100 on EUD2 may acknowledge back to EUD1 successful receipt 482 of the matrix barcode, which may prompt the PIES 100 on EUD1 to release ownership 450 of communication with sensor 404, and to terminate such pairing 452. In one embodiment, after EUD2 has established a valid patient to which to assign sensors, the PIES 100 on EUD2 may transmit to the PIES 100 on EUD1 a ready-to-receive patient sensors signal.

EUD2 may decode the sensor matrix barcode and use the resultant communication information to poll 484 for the sensors being passed by EUD1 (in the example case, sensor 404). After the sensor 404 acknowledges availability 407 to communicate (e.g., pairing with EUD1 is terminated 452), EUD2 may initiate pairing 486 to establish ownership of a new data communication channel with the sensor 404. For example, and without limitation, the PIES 100 on EUD2 may prompt its user for permission to establish connection to the specified sensor through programmatic system file manipulation (e.g., modifying EUD2 system's pair device connection system files). When pairing is complete, the sensor 404 may initiate data streaming 409 (e.g., passing of vital signs collected from Patient 'A' to EUD2 for collection and/or further processing). At Block 490, EUD2 may update the cloned Patient 'A' record to associate available sensors (in the example, sensor 404) with that cloned record.

Figure 5:
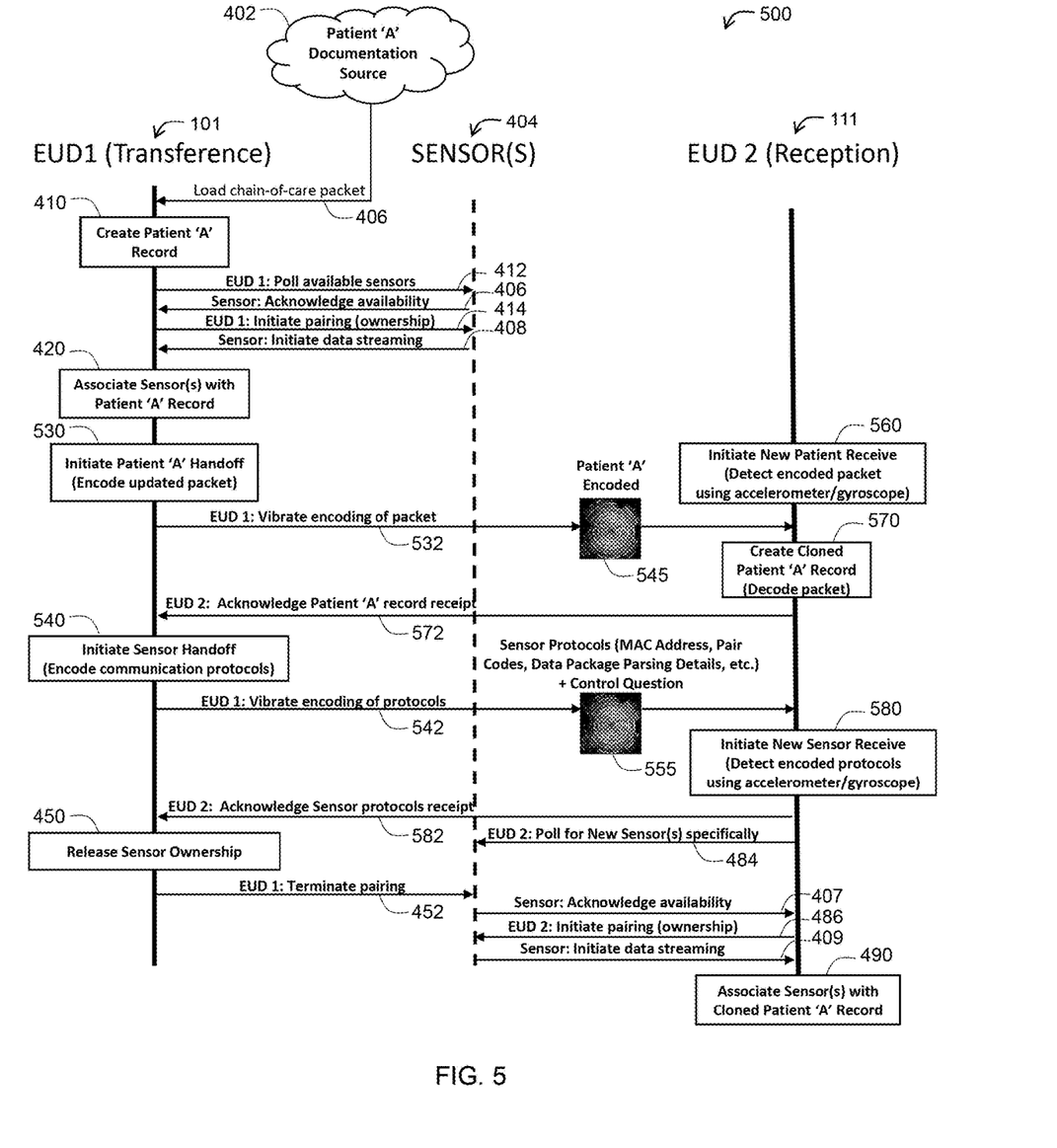
FIG. 5 is a system level communication diagram illustrating haptic pulse-based interaction among components of the PIES of FIG. 1.

Referring now to FIG. 5, an embodiment of the present disclosure involving a haptic pulse encoding methodology 500 is described in more detail. Generally speaking, the same process detailed in FIG. 4 for transfer of patient-related information and connected sensor information applies. However, rather than employ matrix barcode encoding, the embodiment illustrated in FIG. 5 may employ haptic pulse encoding. More specifically, at Block 530, EUD1 may initiate passing of patient-related information for Patient 'A' onto another device, system, and/or personnel by using the PIES 100 on EUD1 to generate a haptic pulse comprising pertinent data from the updated chain-of-care packet for Patient 'A' and may transmit through vibration 532 the encoded data haptic pulse 545 through the EUD1 interface (e.g., smartphone actuator).

Still referring to FIG. 5, a user of the PIES 100 executed on EUD2 may initiate (at Block 560) reception of a subject patient(s) information from EUD1 via use of an EUD2 interface (e.g., accelerometer) to detect the haptic pulse containing, in the illustrated example, the encoded chain-of-care packet for Patient 'A'. For example, and without limitation, the PIES 100 on EUD2 may acknowledge back to EUD1 successful receipt 572 of the haptic pulse, and/or may prompt its user for permission to create a new patient data record after successful detection of EUD1's haptic pulse. Given appropriate permissions, the PIES 100 on EUD2 may decode the haptic pulse and create from it a cloned Patient 'A' record that may comprise some subset of the original chain-of-care packet gathered on EUD1 (Block 570).

Similar to FIG. 4, for example, and without limitation, the PIES 100 on EUD1 may prompt its user to ask if connected sensors for Patient 'A' are to be transferred as well. If so, at Block 540 the PIES 100 on EUD1 may collect all sensor configuration data needed to transfer ownership of data communication with, in the example case, sensor 404 to EUD2. Upon user approval, the PIES 100 on EUD1 may then generate a sensor haptic pulse (Block 540) comprising sensor configuration details/protocols and may transmit through vibration 542 the encoded sensor haptic pulse 555 on the EUD1 interface (e.g., smartphone actuator).

The user of the PIES 100 executed on EUD2 may initiate (at Block 580) reception of the transferring sensor configuration information from EUD1 via use of the EUD2 interface (e.g., accelerometer) to detect through vibration the sensor haptic pulse containing, in the illustrated example, the configuration/protocol information for sensor 404. For example, and without limitation, the PIES 100 on EUD2 may acknowledge back to EUD1 successful receipt 582 of the sensor haptic pulse, which may prompt the PIES 100 on EUD1 to release ownership 450 of communication with sensor 404, and to terminate such pairing 452.

Figure 6:
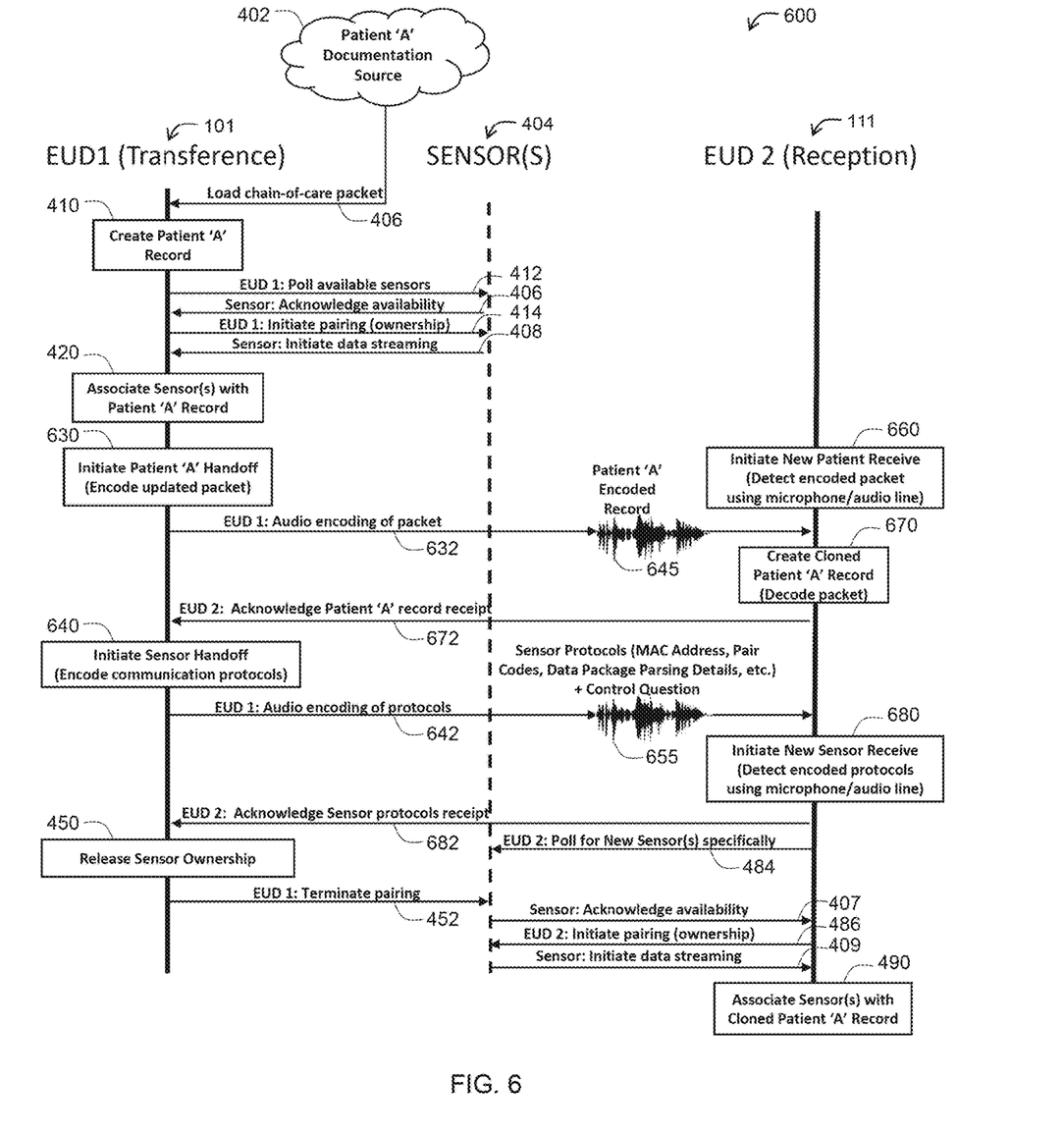
FIG. 6 is a system level communication diagram illustrating audio wave-based interaction among components of the PIES of FIG. 1.

Referring now to FIG. 6, an embodiment of the present disclosure involving an audio encoding methodology 600 is described in more detail. Generally speaking, the same process detailed in FIGS. 4 and 5 for transfer of patient-related information and connected sensor information applies. However, rather than employ matrix barcode encoding or haptic pulse encoding, the embodiment illustrated in FIG. 6 may employ audio encoding. More specifically, at Block 630, EUD1 may initiate passing of patient-related information for Patient 'A' onto another device, system, and/or personnel by using the PIES 100 on EUD1 to generate an audio wave comprising pertinent data from the updated chain-of-care packet for Patient 'A' and may transmit through sound transmission 632 the encoded data audio wave 645 through the EUD1 interface (e.g., smartphone speaker).

Still referring to FIG. 6, a user of the PIES 100 executed on EUD2 may initiate (at Block 660) reception of a subject patient(s)' information from EUD1 via use of an EUD2 interface (e.g., microphone) to detect the sound wave containing, in the illustrated example, the encoded chain-of-care packet for Patient 'A'. For example, and without limitation, the PIES 100 on EUD2 may acknowledge back to EUD1 successful receipt 672 of the sound wave, and/or may prompt its user for permission to create a new patient data record after successful detection of EUD1's sound wave. Given appropriate permissions, the PIES 100 on EUD2 may decode the sound wave and create from it a cloned Patient 'A' record that may comprise some subset of the original chain-of-care packet gathered on EUD1 (Block 670).

Similar to FIGS. 4 and 5, for example, and without limitation, the PIES 100 on EUD1 may prompt its user to ask if connected sensors for Patient 'A' are to be transferred as well. If so, at Block 640 the PIES 100 on EUD1 may collect all sensor configuration data needed to transfer ownership of data communication with, in the example case, sensor 404 to EUD2. Upon user approval, the PIES 100 on EUD1 may then generate a sensor sound wave (Block 640) comprising sensor configuration details/protocols and may transmit through sound wave 642 the encoded sensor sound wave 655 on the EUD1 interface (e.g., smartphone microphone).

The user of the PIES 100 executed on EUD2 may initiate (at Block 680) reception of the transferring sensor configuration information from EUD1 via use of the EUD2 interface (e.g., microphone) to detect the sensor sound wave pattern containing, in the illustrated example, the configuration/protocol information for sensor 404. For example, and without limitation, the PIES 100 on EUD2 may acknowledge back to EUD1 successful receipt 682 of the sensor sound wave, which may prompt the PIES 100 on EUD1 to release ownership 450 of communication with sensor 404, and to terminate such pairing 452.

As described above and illustrated in FIGS. 4, 5, and 6, a person of skill in the art will immediately recognize that the present disclosure may be deployed using a variety of encoded data transfer methodologies including, but not limited to, matrix barcode, haptic pulse, audio wave, data matrix, strobe flash, and infrared. Employment of any encoding scheme that defies reading with the human eye may advantageously provide resistance to electronic eavesdropping through the features of proximity, line-of-sight, and minimized emanations.

Various embodiments of the present disclosure may include features that operate to crisply manage the sensor handoff process, for both signal security and data integrity purposes. For example, and without limitation, the PIES 100 on EUD2 may be configured to scan the sensor handoff Matrix Barcode on EUD1 and may execute/load new system data information and may refresh/execute new code. EUD2 may then notify EUD1 that new system connection code is active, and that EUD2 is therefore ready for EUD1 to release connection to paired medical sensors so that EUD2 may establish ownership of the sensors currently owned by EUD1. The users of EUD1 and EUD2 may be prompted with a final verification of medical sensor handoff action. EUD1 (as owner of the transferring sensor) may display a session handoff verification code on its display along with options to authenticate through alternative means such as audio and/or wired (i.e., USB) and/or wireless (i.e., NFC). For example, and without limitation, Audio Verification (either wired or wireless) may send a series of frequency, duration, and intensity-based codes representing 0-9 characters for the receiving device to "learn" session handoff audio codes. EUD2 (as receiver of the transferring sensors) may enter the required session handoff verification code and EUD1 may release (i.e., unpair, programmatically or manually, ownership of the transferring sensors) and EUD2 may pair to previously paired but now available patient medical sensors. Confirmation of successful or unsuccessful handoff may be presented to EUD1 and EUD2 users.

In another embodiment, also for example, and without limitation, the PIES 100 on EUD1 may augment sensor connection details with specific EUD1 user information encoded in the sensor handoff matrix code that is unique to EUD1 user (i.e., biometric data, passcode/PIN, Question & Answer) for authentication. When the EUD2 user scans the displayed EUD1 sensor handoff matrix code, a dialog may be presented on EUD2's screen that may request embedded matrix authentication details. If the EUD2 user correctly enters authentication information as embedded in the sensor handoff matrix barcode, then the EUD2 may notify the EUD1 via a message exchange such as, for example, but not limited to, a return scannable matrix code which may place the EUD2 into search mode for sensors detailed in the embedded sensor handoff matrix barcode. Once the EUD1 receives authenticated handoff, the EUD1 may release its connection to subject patient medical sensors and may close subject patient files (e.g., by manually authentication through "bumping" the devices and initiating the NFC awareness communication method that is used as a physical handshake).

It will be appreciated that the systems and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another implementation, any of the systems and methods described above may be embodied in any suitable transmission or propagation medium carrying computer-executable code and/or any inputs or outputs from same.

What is claimed is:

1. A method of offline data transfer using between a transference device and a reception device, the method comprising:
   encoding a data package with a transference device, wherein the data package comprises patient real-time health information wherein the patient real-time health information is stored in the transference device;
   compressing the data package with the transference device;

encrypting the data package with the transference device;

encrypting a data package representation of the encrypted data package with the transference device, wherein the data package representation comprises one or more of a matrix barcode, a QR code, a haptic pulse, and an audio tone;

presenting the data package representation offline with the transference device;

receiving the data package representation offline with a reception device with one or more of a camera, an accelerometer, and a microphone;

decrypting the data package representation with the reception device;

decompressing the data package representation with the reception device; and decoding the data package representation offline with the reception device, wherein the data package is stored in with the reception device, wherein the decoding the data package saves the patient real-time health information to the reception device.

\* \* \* \* \*